United States Patent [19]

Mawhirt et al.

[11] Patent Number: 5,630,828

[45] Date of Patent: May 20, 1997

[54] LOW COST DISPOSABLE LANCET

[75] Inventors: James A. Mawhirt, Brooklyn, N.Y.; Anthony F. Kuklo, Jr., Bridgewater, N.J.; Donald Foggia, Ocean, N.J.; Donald W. Allen, Point Pleasant, N.J.

[73] Assignee: International Techndyne Corporation, Edison, N.J.

[21] Appl. No.: 633,625

[22] Filed: Apr. 17, 1996

[51] Int. Cl.$^6$ ................................................ A61B 17/32
[52] U.S. Cl. ........................................... 606/187; 128/770
[58] Field of Search .............................. 606/181–183; 128/770, 771

[56] References Cited

U.S. PATENT DOCUMENTS

| | | |
|---|---|---|
| 3,760,809 | 9/1973 | Campbell, Jr. . |
| 4,539,988 | 9/1985 | Shirley et al. ............... 606/182 |
| 4,553,541 | 11/1985 | Burns . |
| 5,133,730 | 7/1992 | Biro et al. . |
| 5,212,879 | 5/1993 | Biro . |
| 5,395,388 | 3/1995 | Schraga . |

*Primary Examiner*—Michael Buiz
*Assistant Examiner*—William Lewis
*Attorney, Agent, or Firm*—Plevy & Associates

[57] ABSTRACT

A low cost safety lancet device for creating a skin incision. The lancet contains a unitarily formed plastic body, thereby making the lancet device easy to manufacture at a low cost. The lancet device includes a housing having an internal hollow and a blade beam pivotally disposed within the hollow of the housing for generating an incision in a patient's skin. Upon the activation of the device, the blade beam pivots through a predetermined path which causes a blade associated with the blade beam to travel out of an aperture in the housing to incise the patient's skin. The device further includes a trigger for propelling the blade through the path and a cam projection disposed within the housing which cooperates with the trigger to accelerate the trigger through the hollow of the housing thereby causing the blade to accelerate through the aperture of the housing. A portion of the trigger then unavoidably deflects to automatically allow the blade to retract back into the hollow of the casing after incising the patient's skin.

24 Claims, 4 Drawing Sheets

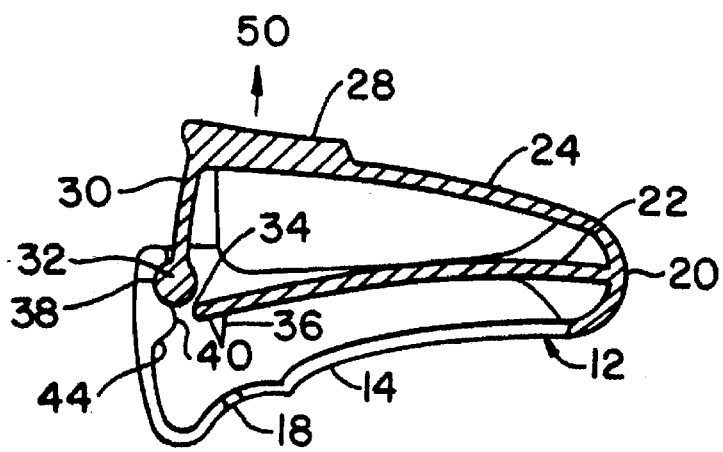
FIG. 2A
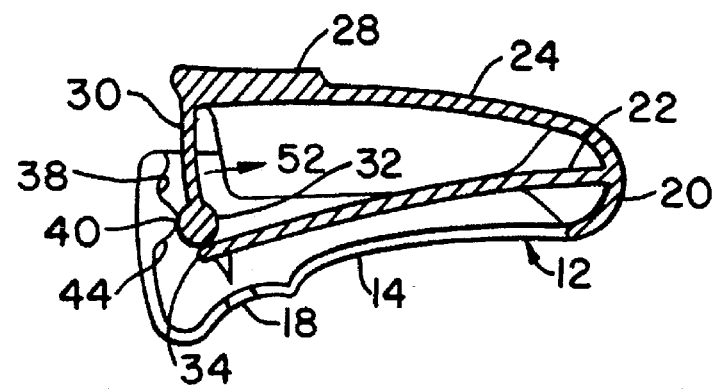
FIG. 2B
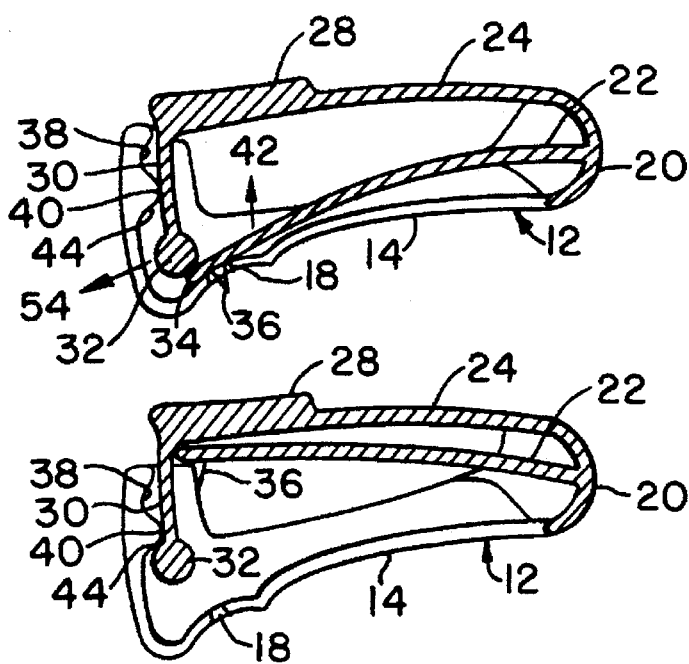
FIG. 2C
FIG. 2D

LOW COST DISPOSABLE LANCET

RELATED APPLICATIONS

International Technidyne Corporation, the assignee herein, is record owner of U.S. patent application Ser. No. 08/465,686 entitled SELF ACTIVATED FINGER LANCET filed by James Mawhirt et al. on Jun. 6, 1995 and U.S. patent application Ser. No. 08/549,173entitled LOW COST DISPOSABLE LANCET filed by James Mawhirt et at. on Oct. 27, 1995.

FIELD OF THE INVENTION

The present invention relates generally to blood drop generator devices and more particularly to a low cost disposable safety lancet device with a lancet triggering mechanism that is easy and inexpensive to manufacture and assemble.

BACKGROUND OF THE INVENTION

Blood drop generation devices also known as lancet devices, generate blood samples for use in performing various blood tests. Such devices create a small puncture or incision in the skin of the fingertip, although the puncture or incision can be made in other areas of the body such as the foot, arm, or leg.

Many prior art lancet devices employ spring loaded cutting blades enclosed within a casing or housing. The housing of the device is placed against the skin and the blade is released by a triggering mechanism in the device. The potential energy stored within the spring causes the blade to exit the housing to create a uniform puncture or incision in the skin which can be controlled in terms of location, depth, and sterility. Since the blade is concealed within the housing, the patient is unable to view the blade prior to, during, or after the puncturing of the skin which reduces the patient's anxiety.

Many of these prior art lancet devices are marketed as "safety" lancet devices because they include means for retracting the blade back into the housing after the puncture or incision has been made which advantageously reduces the danger a disease being spread through contact with the used blade of the device. This is an important feature since deadly viruses such as AIDS and Hepatitis can spread from accidental punctures obtained from lancets used previously on an infected patient. However, some of these "safety" devices are not truly safe in that the blade can be pushed out or accessed after use.

Another feature common to many prior art lancet devices is the use of a plunging cutting motion. More specifically the cutting blades are adapted to be plunged through the skin in a motion which is perpendicular to the skin. This produces an incision which matches the size of the cutting blade. Such lancets are exemplified by U.S. Pat. No. 5,133,730 issued on Jul. 28, 1992 to Biro, entitled DISPOSABLE RETRACTABLE FINGER STICK DEVICE AND METHOD FOR MAKING THE SAME and assigned to International Technidyne Corporation the assignee herein. In the Biro patent, a sharp blade is provided on a spring biased pivot arm which moves the blade out through an orifice in the lancet housing and then retracts the blade back into the housing. Although the blade is positioned on a pivot arm, the blade is directed perpendicularly into the surface of the skin. The shape of the blade helps the blade enter the skin and make the needed incision.

Other lancet devices that create plunge cuts are exemplified in U.S. Pat. No. 3,760,809 to Cambell, Jr. entitled SURGICAL LANCET HAVING CASING and U.S. Pat. No. 5,395,388 to Schrage, entitled SINGLE UNIT LANCET DEVICE.

In order to lower the manufacturing costs of lancet devices, designs with only two or three separate parts have been developed. Such designs generally employ a cutting blade held by a complex molded structure that both advances and retracts the blade. Examples of this type of lancet device design are shown in U.S. Pat. No. 4,553,541, entitled AUTOMATIC RETRACTABLE LANCET ASSEMBLY, to Burns, and U.S. Pat. No. 5,212,879, entitled METHOD FOR MANUFACTURING A DISPOSABLE-RETRACTABLE FINGER STICK DEVICE to Biro et al., which is assigned to International Technidyne Corp., the assignee herein. Although such lancet devices have fewer parts than earlier designs, they still tend to be relatively expensive to produce due to the complex nature of the tooling which requires frequent cleaning and maintenance, and the close tolerance nature of the parts. Accordingly, a substantially high percentage of rejected parts and significant downtime are associated with these prior art designs. Hence the cost of such lancet devices remain relatively high.

In many prior art lancet devices, expensive metal springs are used. In some designs the springs form a portion of the cutting blade. In other designs, the cutting blade is driven by the spring. In both cases, the springs add significantly to the overall cost of the lancet as well to the complexity of assembling the lancet with the spring in its compressed, ready-to-use orientation.

Accordingly there is need for a disposable safety lancet that eliminates the metal spring and which is relatively inexpensive to manufacture. There is a further need for a disposable safety lancet that addresses the full time safety issue by providing a triggering mechanism that once activated to propel the blade out and then into the case, cannot be reactivated or otherwise manipulated to cause the blade to be extended out of the case.

SUMMARY OF THE INVENTION

A safety lancet device including a housing having an internal hollow and a blade beam pivotally disposed within the hollow of the housing for generating an incision in a patient's skin. Upon the activation of the device, the blade beam pivots through a predetermined path which causes a blade associated with the blade beam to travel out of an aperture in the housing to incise the patient's skin. The device includes a trigger for propelling the blade through the path and a cam projection disposed within the housing which cooperates with the trigger to accelerate the trigger through the hollow of the housing thereby causing the blade to accelerate through the aperture of the housing. A portion of the trigger then deflects to allow the blade to retract back into the hollow of the casing after incising the patient's skin.

BRIEF DESCRIPTION OF THE DRAWINGS

For a detailed understanding of the present invention, reference should be made to the following detailed description taken in conjunction with the accompanying drawings wherein:

FIG. 2A is a cross-sectional side view of the lancet device of the present invention assembled in a loaded-ready to use position;

FIG. 2B is a cross-sectional side view of the lancet device of FIG. 2A immediately after triggering;

FIG. 2C is a cross-sectional side view of the lancet device of FIG. 2A showing the blade beam at cutting depth;

FIG. 2D is a cross-sectional side view of the lancet device of FIG. 2A after the cutting blade has automatically retracted;

DETAILED DESCRIPTION OF THE DRAWINGS

Figure 1A:
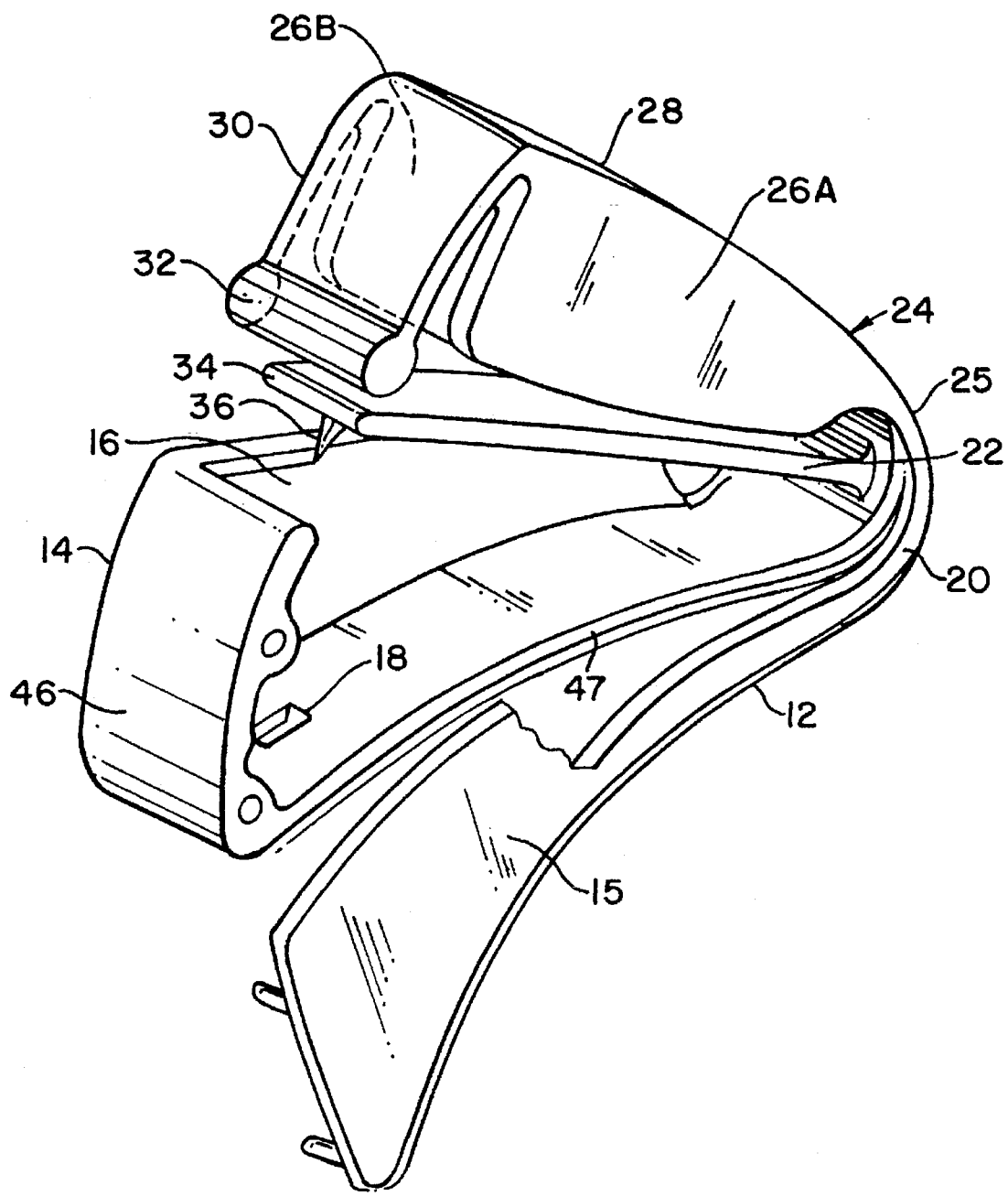
FIG. 1A is an as molded perspective view of the lancet device of the present invention.
Figure 1B:
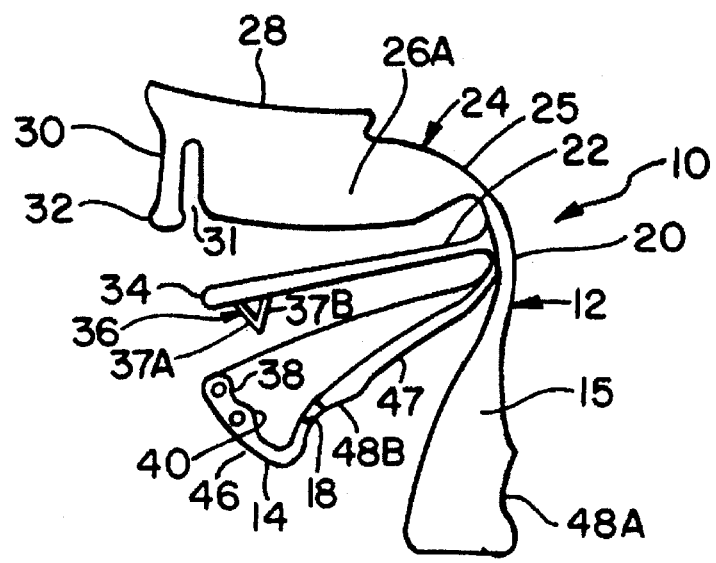
FIG. 1B is an as molded side elevational view of the lancet device of the present invention.

Referring to FIGS. 1A and 1B, the lancet device 10 of the present invention is shown in an "as molded" condition. The lancet device 10 is essentially comprised of only two parts, a molded plastic body 12 and a metallic cutting blade 36. Alternatively, the lancet device 10 can be comprised of a single unitary plastic part molded from a single plastic material, two co-injected plastic materials or two stage injected plastic materials, where the cutting blade 36 is molded from the same or one of the two co-injected or two stage injected plastic materials and the plastic body 12 is molded from the same or the other of the two co-injected or two stage injected plastic materials. In any case, the plastic body 12 includes a resilient spring loop 20, a housing 14 section and a housing sidewall section 15 which both extend from one end of the resilient spring loop 20, a resilient blade beam 22 which extends from the inner surface of the spring loop 20, and a trigger 24 which extends from the other end of the resilient spring loop 20.

The housing section 14 and the housing sidewall section 15 are adapted to be snapped together when the lancet device 10 is assembled to keep the cutting blade 36 sterile and to prevent accidental contact with the cutting blade 36. The housing section 14 includes an end wall 46 and a base wall 47. A concave indent 48B is optionally provided in the base wall section 47 of the housing section 14 and a corresponding concave indent 48A is provided in the housing sidewall section 15. The indents 48A and 48B adapt the lancet device 10 to the curved surface of a fingertip. In other embodiments of the lancet device of the present invention, the indents can be omitted so that the lancet device can be used on flatter areas of the body.

The assembled housing section 14 and the housing sidewall section 15 define an open hollow 16 which encases the blade beam 22. An aperture 18 is disposed at the apex of the indent 48B in the basewall 47 of the housing section 14. The aperture 18 allows the cutting blade 36 to emerge from the hollow 16 when the lancet device 10 is triggered. The inner surface of the end wall 46 defines a cylindrical detent 38 and a cylindrical cam 40.

The blade beam 22 extending centrally from the inner surface of the resilient spring loop 20, terminates at a rounded free end 34. The cutting blade 36 is disposed marginally adjacent to the free end 34 of the blade beam 22. Preferably, the blade 36 is triangular in shape with two sharpened edges 37A and 37B as shown in FIG. 1B. In FIGS. 1A and 1B, the cutting blade 36 is a separate metal piece that is molded into the blade beam or otherwise mechanically or adhesively anchored thereto. Alternatively, the cutting blade 36 is a unitary plastic portion of the blade beam 22 as mentioned earlier.

The trigger 24 includes a top surface 25 and a pair of spaced apart cutting blade shields 26A and 26B which extend into the hollow 16 defined by the assembled housing section 14 and the housing sidewall section 15 to prevent contact with the cutting blade 36 along with a connecting member 30 that extends down from the free end of the trigger 24. The connecting member 30 includes a cylindrically shaped cam follower 32 formed at the end thereof. A slot 31 separates the connecting member 30 from the cutting blades shields 26A and 26B. The slot 31 allows the connecting member 30 to resiliently deflect as the cam follower 32 slides over the cam 40 as will be explained. The trigger 24 also includes a thumb rest 28 which is molded into the top surface 25 thereof.

Figure 4:
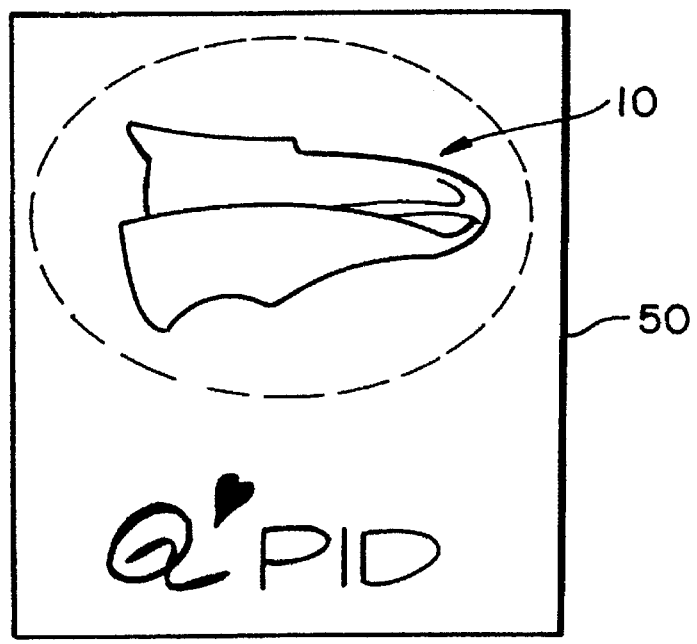
FIG. 4 is side elevational view of the lancet device of the present invention in the loaded-ready to use position and packaged in a blister pack.

The lancet device 10 is preferably packaged in a blister pack 50 as shown in FIG. 4. Before packaging, the lancet device 10 is assembled into a loaded position where it is ready to create an incision in skin.

FIGS. 2A–2D depict the operation of the lancet device 10. FIG. 2A shows the lancet device 10 locked in the loaded position. As shown, the cam follower 32 is seated in the detent 38 defined by the housing section 14 which locks the trigger 24 in the loaded positioned while the resilient spring loop 20 biases the trigger 24 in the direction of arrow 50 as the spring loop 20 tries to open into a more flat orientation. On the other hand, the resilient blade beam 22 rests in an unbiased position within the hollow 16 defined by the housing section 14 and the sidewall section 15.

A user grips the lancet device 10 between the finger to be incised and the thumb of the same hand so that the indents 48A and 48B abut against the skin of the finger in the area where the incision is to be made and the thumb rests on the thumb rest 28. The thumb and the finger are then thrust together to activate the lancet device 10. When the trigger 24 is pressed down, the cam follower 32 rides up along the cam 40 which causes the connecting member 30 to deflect in the direction of arrow 52. When the cam follower 32 reaches the high point of the cam 40 to fully deflect the connecting member 30, the cam follower 32 makes contact with the free end 34 of the resilient blade beam 22. This results in a maximum buildup of spring bias force which creates a predetermined resistance. This causes the user to apply a sufficient amount of trigger pressure to overcome this resistance.

In FIG. 2C, the user has applied the requisite trigger pressure to overcome the predetermined resistance which accelerates the free end 34 of the blade beam 22 including the cutting blade 36 down through the housing section 14 where the cutting blade 36 passes through the aperture 18 and into the skin. When the free end 34 of the blade beam 22 engages the bottom surface of the housing section 14 automatic retraction of the cutting blade 36 is initiated. In particular, as the accelerated downward travel of the trigger 24 continues, the connecting member deflects the cam follower 32 away from the blade beam 22 in the direction of arrow 54 which forces the cam follower 32 to slide off the free end 34 of the blade beam 22. This allows the resilient blade beam 22, which is now biased in the direction of arrow 42, to automatically retract the cutting blade 36 back into the housing section 14 as shown in FIG. 2D.

When the user releases the trigger 24, the cam follower 32 allows the biased trigger 24 to travel partially up through the housing section 14 into an unloaded trigger position whereby the cam follower 32 engages a trailing portion 44 of the cam 40. With the trigger 24 in the unloaded position and the cutting blade 36 fully concealed within and protected from contact by the housing section 14 and the housing sidewall section 15, the lancet device 10 can be discarded.

Figure 3A:
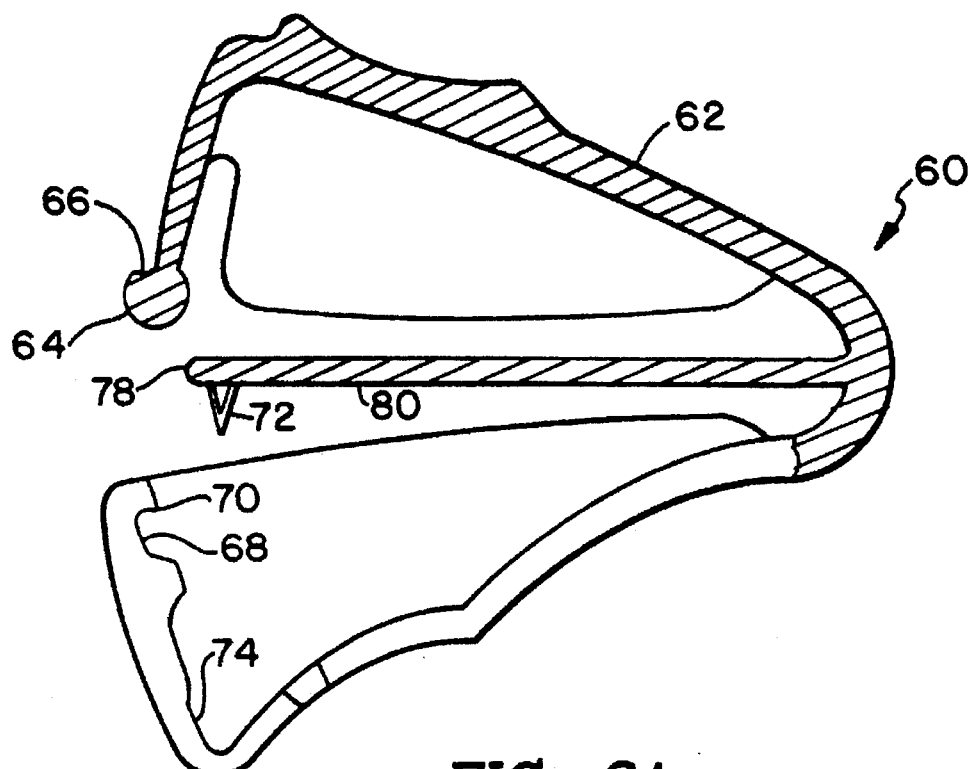
FIG. 3A is an as molded cross-sectional side view of another embodiment of the lancet device of the present invention.
Figure 3B:
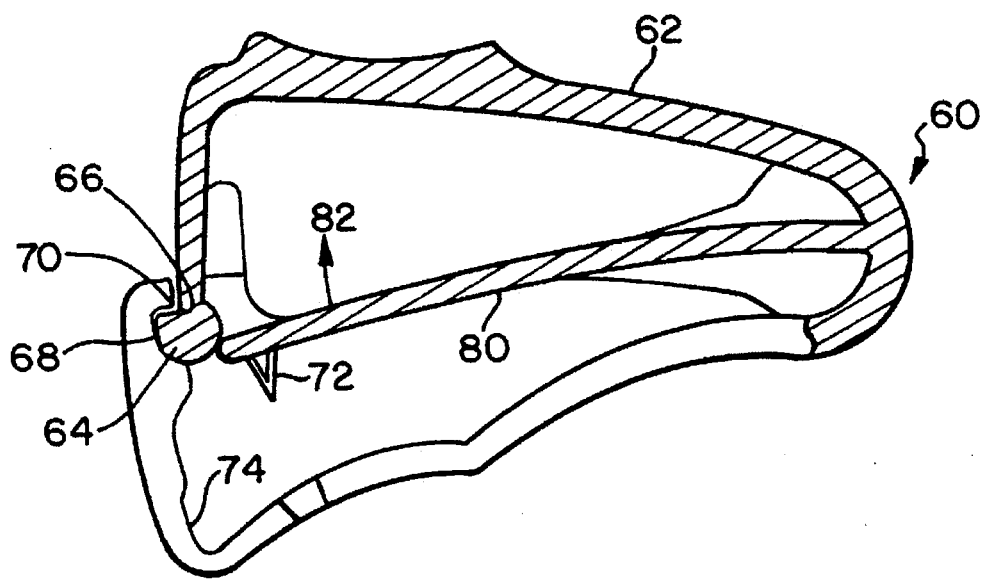
FIG. 3B is a cross-sectional side view of the lancet device of FIG. 3A assembled in a loaded-ready to use position.

Referring to FIGS. 3A and 3B, there is shown an alternative embodiment of the lancet device of the present invention designated by numeral 60. The lancet device 60 includes a few features not shown in the first embodiment. In particular, the trigger 62 has a cam follower 64 with a groove 66 which receives a hook member 70 formed at the top of the detent 68. The hook and groove arrangement advantageously assures that the cam follower 64 will not accidentally disengage from the detent 68, thus, causing the lancet device 60 to return to the "molded" position from the "loaded" position which would result in the exposure of the cutting blade 72. Further, the blade beam 80 is adapted to make contact with the trigger and be biased in the direction of arrow 82 when the lancet device 60 is in the "loaded" position in order provide a more linear buildup of trigger resistance. Further, the inner surface of the housing includes a recess 74 which allows the cam follower 64 to be deflected sufficiently away from the free end 78 of the blade beam 80 to automatically retract the cutting blade 72 back into the housing.

It should be understood that the embodiments described herein are merely exemplary and that a person skilled in the art may make many variations and modifications to the disclosed embodiments utilizing functionally equivalent elements to those described herein. For example, the housing sidewall section can be omitted to provide a full operator view of the blade and beam assembly. Any and all such variations or modifications as well as others which may become apparent to those skilled in the art, are intended to be included within the scope of the invention as defined by the appended claims.

What is claimed is:

1. A safety lancet device, comprising:
   a housing having an aperture and a cam disposed on the inner surface of said housing;
   a trigger coupled to said housing, said trigger being movable relative to said housing between a first position and a second position, said trigger further having a tip positioned relative to said cam such that said tip slides over said cam when said trigger is moved from said first position to said second position;
   a beam member including a cutting blade, enclosed within said housing and pivotally coupled thereto, said trigger being operative for moving said blade through said aperture when said trigger is moved from said first position to said second position; and
   wherein said cam provides a predetermined measure of resistance to the movement of said trigger from said first position to said second position, wherein a user applying a force to said trigger which is sufficient to overcome said predetermined measure of resistance causes said tip of said trigger to slide over said cam and further causes said blade to accelerate through said aperture of said housing to incise the user's skin; and
   wherein said trigger includes blade retracting means for automatically allowing said blade to retract back into said housing after incising the user's skin independent of the user's interaction.

2. The device according to claim 1, further including a spring element for biasing said arm element into said first position.

3. The device according to claim 1, wherein said housing, said cam, said trigger, said beam member, and said retractor means are unitarily molded together from a single part thereby substantially minimizing the cost of said safety lancet device.

4. The device according to claim 1, wherein said blade is comprised of metal material.

5. The device according to claim 1, wherein said blade is comprised of a plastic material.

6. The device according to claim 1, wherein said lancet device is molded from a plastic material.

7. The device according to claim 1, wherein said housing, said cam, said trigger, said beam member, and said blade are a single unitary member molded from two co-injected plastic materials, wherein one of said co-injected plastic materials forms said blade, and the other of said two co-injected plastic materials forms said housing, said cam, said trigger, and said beam member.

8. The device according to claim 1, wherein said housing, said cam, said trigger, said beam member, and said blade are a single unitary member molded from two stage injected plastic materials, wherein one of said stage injected plastic materials forms said blade, and the other of said two stage injected plastic materials forms said housing, said cam, said trigger, and said beam member.

9. The device according to claim 1, wherein said said trigger further comprises a cam follower disposed on its tip for biasing against said cam and moving said blade through said aperture.

10. The device according to claim 1, further comprising a locking means disposed on the inner surface of said housing for locking said trigger in said first position.

11. A safety lancet device, comprising:
   a housing having an aperture and a cam disposed on the inner surface of said housing;
   trigger coupled to said housing, said trigger being movable relative to said housing between a first position and a second position, said trigger further having a tip positioned relative to said cam on said housing such that said tip slides over said cam when said trigger is moved from said first position to said second position;
   a beam member including a cutting blade enclosed within said housing and pivotally coupled thereto, said trigger being operative for moving said blade through said aperture when said trigger is moved from said first position to said second position; and
   wherein said cam on said housing cooperates with said tip of said trigger to provide a predetermined measure of resistance to the movement of said trigger from said first position to said second position wherein a user applying a force to said trigger which is sufficient to overcome said resistance causes said tip to slide over said cam and further causes said blade to accelerate through said aperture of said housing to incise the user's skin; and
   wherein said housing includes an indent for receiving a portion of a finger, said aperture being disposed with said indent.

12. The device according to claim 11, further comprising a locking means disposed on the inner surface of said housing for locking said trigger in said first position.

13. The device according to claim 12, wherein said locking means includes a detent formed above said cam on said inner surface of said housing, said cam follower engaging said detent when said trigger is in said first position.

14. A safety lancet device comprising:

a housing having an internal hollow and an aperture, said housing further having a cam projection extending into said hollow from said housing;

a blade assembly having a beam and a blade disposed on the beam, said blade assembly being disposed within said hollow of said housing for generating an incision in a patient's skin, wherein upon the activation of said device, said blade assembly follows a predetermined path which causes said blade to travel out of said aperture in said housing to incise the patient's skin and then automatically retract back through said aperture into said hollow of said housing;

blade triggering means for propelling said blade assembly through said path, said blade triggering means further having a tip cooperating with said cam projection such that, upon activation of the device, said tip slides along said cam projection and accelerates through said hollow of said housing thereby causing said blade to accelerate through said aperture of said housing; and retractor means comprising a connecting member disposed between said tip and said blade triggering means which flexes as said blade assembly is projected through said path such that said blade assembly is released from said blade triggering means and said blade automatically retracts back into said housing after incising the user's skin independent of the user's interaction;

wherein said cam projection, said blade assembly, and said blade triggering means cooperate together to control the depth of incision and said blade assembly is not visible before and after use by a user.

15. The device according to claim 14, wherein said blade is comprised of a metal material.

16. The device according to claim 14, wherein said blade is comprised of a plastic material.

17. The device according to claim 14, further comprising blade assembly locking means for preventing inadvertent activation of the device.

18. The device according to claim 17, wherein said blade assembly locking means includes a detent formed adjacent to said cam projection, said detent cooperating with said blade triggering means.

19. The device according to claim 14, wherein said housing, said blade assembly, said blade triggering means, said cam projection, and said retractor means are unitarily molded together.

20. The device according to claim 14, wherein said housing includes first and second enclosing covers which fully conceal said blade and beam.

21. The device according to claim 14, wherein said housing includes first and second sides, said first side having an enclosing cover and said second side having a snap-into-place unitarily molded cover concealing said blade at all times.

22. A safety lancet device, comprising:

a beam having a free end and a cutting blade disposed adjacent its free end;

a first L-shaped member having a straight arm, an end wall, an aperture through its straight arm, and a cam extending from its end wall inwardly toward its straight arm;

a second L-shaped member having a straight arm and a resilient end wall terminating in a tip;

wherein said beam and said L-shaped members are coupled at a common pivot point, wherein said end walls of said L-shaped members project toward each other; said beam is disposed between said straight arms of said L-shaped members, with said free end of said beam remaining exposed; and said blade on said beam faces and is axially aligned with said aperture of said first L-shaped member; and wherein the tip of said second L-shaped member is so disposed relative to said first L-shaped member and said beam such that when a user compresses said L-shaped members toward each other, the tip of said second L-shaped member pushes said free end of said beam toward said first L-shaped member; said tip biases against said cam to provide a predetermined measure of resistance to the movement of said L-shaped members, wherein a user applying a force sufficient to overcome said resistance causes said tip to slide over said cam and further causes said blade to accelerate through said aperture of said first L-shaped member to incise the user's skin; and wherein said resilient end wall of said second L-shaped member upon contacting said first L-shaped member flexes off said free end of said beam to allow said beam to automatically retract toward the straight arm of said second L-shaped member.

23. The device according to claim 22, further comprising sidewalls connected to said straight arms of said L-shaped members for encasing said beam and said blade such that said blade is not visible before and after use by a user.

24. The device according to claim 22, further comprising a locking means disposed on said end wall of said first L-shaped member adjacent said cam for securing said tip of said second L-shaped member against said end wall of said first L-shaped member so that said beam is encased between said L-shaped members.

* * * * *